United States Patent
De Man et al.

(10) Patent No.: US 7,548,604 B2
(45) Date of Patent: Jun. 16, 2009

(54) METHOD AND APPARATUS FOR REDUCTION OF METAL ARTIFACTS IN CT IMAGING

(75) Inventors: Bruno K. B. De Man, Clifton Park, NY (US); Deborah Joy Walter, Terre Haute, IN (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/620,004

(22) Filed: Jan. 4, 2007

(65) Prior Publication Data

US 2008/0165920 A1   Jul. 10, 2008

(51) Int. Cl.
*A61B 6/00* (2006.01)
(52) U.S. Cl. .............................. 378/17; 378/4; 378/207
(58) Field of Classification Search ...................... 378/4, 378/9, 207, 901
See application file for complete search history.

(56) References Cited

U.S. PATENT DOCUMENTS

| 4,305,127 | A  | * | 12/1981 | Heuscher ................... 600/425 |
| 4,333,145 | A  | * | 6/1982  | Heuscher et al. ............ 600/425 |
| 5,115,394 | A  | * | 5/1992  | Walters ...................... 382/131 |
| 5,243,664 | A  | * | 9/1993  | Tuy ............................ 382/130 |
| 5,881,122 | A  | * | 3/1999  | Crawford et al. ............... 378/4 |
| 6,229,869 | B1 | * | 5/2001  | Hu ................................. 378/4 |
| 6,504,892 | B1 | * | 1/2003  | Ning ............................. 378/4 |
| 6,507,633 | B1 | * | 1/2003  | Elbakri et al. .................. 378/8 |
| 6,529,575 | B1 | * | 3/2003  | Hsieh ............................ 378/4 |
| 6,580,777 | B1 | * | 6/2003  | Ueki et al. .................... 378/17 |
| 6,754,298 | B2 | * | 6/2004  | Fessler ......................... 378/4 |
| 7,023,951 | B2 |   | 4/2006  | De Man |
| 2005/0226484 | A1 | * | 10/2005 | Basu et al. ................. 382/131 |
| 2005/0249416 | A1 | * | 11/2005 | Leue et al. ................. 382/195 |
| 2006/0203956 | A1 | * | 9/2006  | Raupach ........................ 378/4 |

\* cited by examiner

*Primary Examiner*—Edward J Glick
*Assistant Examiner*—Alexander H Taningco
(74) *Attorney, Agent, or Firm*—Jason K. Klindtworth

(57) ABSTRACT

A method and apparatus for reducing artifacts in image data generated by a computed tomography system is provided. The artifacts are due to the presence of a high density object in a subject of interest. CT data is acquired at a number of differing tilt angles. The data is then combined and reconstructed to generate an improved composite image substantially free of artifacts caused by the high density object.

16 Claims, 3 Drawing Sheets

METHOD AND APPARATUS FOR REDUCTION OF METAL ARTIFACTS IN CT IMAGING

BACKGROUND OF THE INVENTION

The present invention generally relates to the field of image reconstruction in computed tomography (CT) systems and more particularly to a method and apparatus for reducing artifacts in image data caused by high density objects.

CT scanners operate by projecting fan shaped or cone shaped X-ray beams through an object. The X-ray beams are generated by an X-ray source, and are generally collimated prior to passing through the object being scanned. The attenuated beams are then detected by a set of detector elements. The detector elements produce a signal based on the intensity of the attenuated X-ray beams, and the signals are processed to produce projections. By using reconstruction techniques, such as filtered backprojection, useful images are formed from these projections.

A computer is able to process and reconstruct images of the portions of the object responsible for the radiation attenuation. As will be appreciated by those skilled in the art, these images are computed by processing a series of angularly displaced projection images. This data is then reconstructed to produce the reconstructed image, which is typically displayed on a cathode ray tube, and may be printed or reproduced on film.

One problem with reconstructed images in CT systems is artifacts caused by the presence of high density objects, for example, metal objects in a subject. The presence of such high density objects in a subject causes relatively high attenuation of the X-ray beams as they propagate through the subject, thereby resulting in a reconstructed image with artifacts. These artifacts can produce significant dark and bright streaks in the reconstructed image that severely limit the CT assessment of soft tissue and bone structures surrounding the high density objects. The artifacts are due to one or more effects such as beam hardening, poor signal-to-noise ratio, scattered radiation, partial volume effect, aliasing, and object motion.

Different solutions for metal artifacts reduction have previously been employed. For example, when a small metallic object is present in a scan, such as a metallic tooth filling or crown, adaptive filtration or interpolation methods are often applied on the sinogram domain of CT data, as the degrading effect of the metallic filling/crown is not very significant. For metallic objects significantly larger in size, such as a metal knee or prosthetic hip, the degrading effect increases and other reconstruction methods must be employed. One of these methods uses a polynomial model to address the increased beam hardening effect. Polynomial correction also has its limits however, as it works well only when the high density object in the patient is comprised of a homogenous material. As such, iterative algorithms are sometimes implemented, such as an EM (expectation maximization)-type algorithm or other iterative methods which incorporate beam hardening and other physical effects in the forward model.

A disadvantage of all the above techniques is that they result in either only a partial reduction of artifacts, introduce new artifacts, have a high computation time, or result in the formation of blurred images. Therefore, a need exists for a method of reducing or eliminating metal artifacts in CT imaging in a computationally-efficient, dose-efficient, and robust manner. Such a method would be able to accommodate high density objects of various sizes and compositions.

BRIEF DESCRIPTION OF THE INVENTION

The present invention recites a method and apparatus for reducing artifacts in image data caused by high density objects.

Therefore, in accordance with one aspect of the present invention, a computer readable storage medium includes a computer program to adaptively control a CT system for reconstructing an image with reduced artifacts caused by a high density object in a scanned region of interest. The computer program represents a set of instructions that, when executed by a computer, causes the computer to perform a plurality of x-ray scans at a plurality of tilt angles, acquire a plurality of projection data sets from the plurality of x-ray scans, combine the plurality of projection data sets, and reconstruct a composite image from the combined image data sets.

In accordance with another aspect of the present invention, a method of reducing metal artifacts in CT imaging includes the steps of acquiring CT projection data of a region of interest at each of a number of differing irradiation angles, and combining the CT projection data acquired at each of the number of different irradiation angles so as to reduce metal artifacts in a resulting image.

In accordance with yet another aspect of the present invention, a CT imaging system to reduce metal artifacts includes a CT imaging apparatus. The CT imaging apparatus has a data acquisition module that includes a gantry having a bore designed to receive a patient therethrough, and wherein the gantry has at least one x-ray source and an x-ray detector disposed therein to emit x-rays toward the patient and receive x-rays attenuated by the patient, respectively. The CT imaging apparatus further includes a computer programmed to acquire CT projection data at a number of tilt angles and merge the CT projection data to create an aggregate image. The merging of the projection data is based on one of a variance map, morphological operations, and an iterative reconstruction process.

Various other features and advantages of the present invention will be made apparent from the following detailed description and the drawings.

BRIEF DESCRIPTION OF THE DRAWINGS

The drawings illustrate one embodiment presently contemplated for carrying out the invention.

In the drawings.

DETAILED DESCRIPTION OF THE INVENTION

Figure 1:
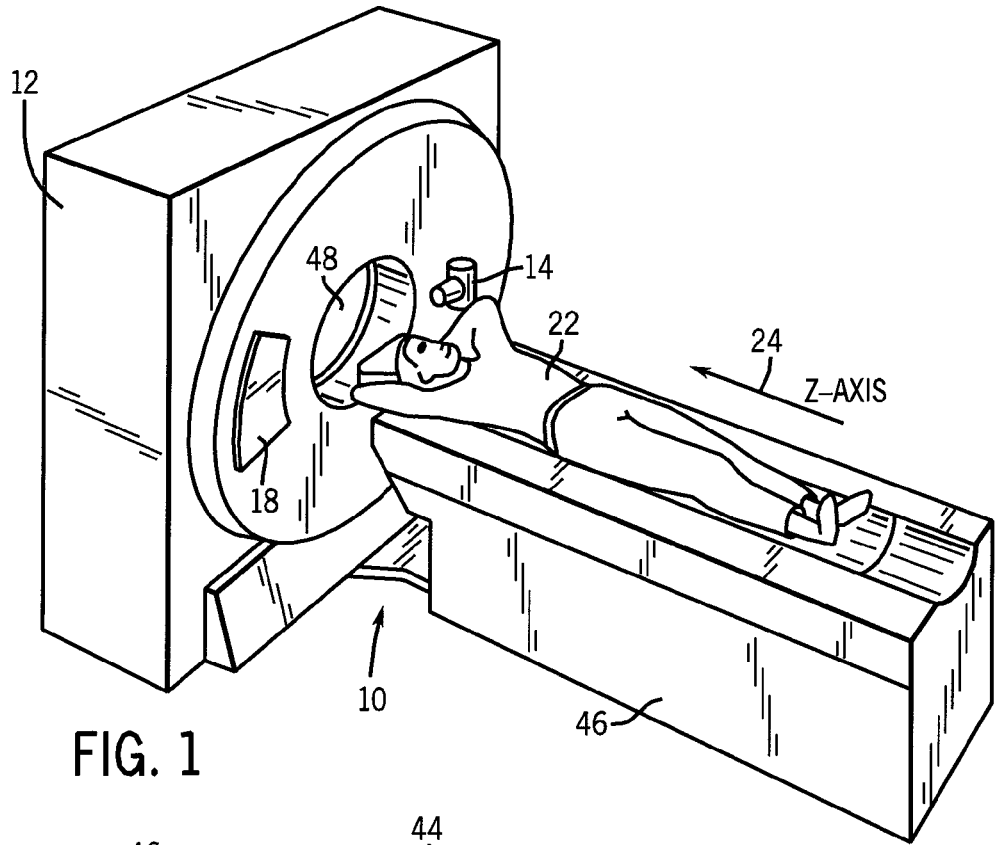
FIG. 1 is a perspective view of a computed tomography (CT) imaging system according to one embodiment of the present invention.
Figure 2:
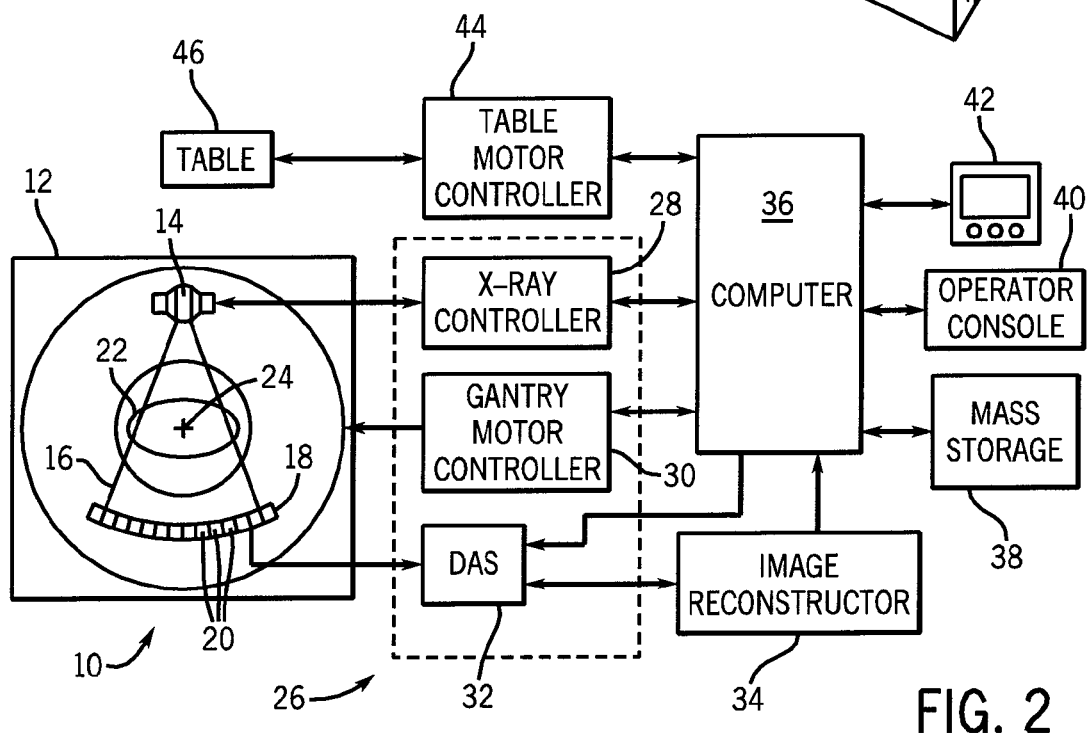
FIG. 2 is a schematic of the CT imaging system of FIG. 1.

Referring to FIGS. 1 and 2, an embodiment of a computed tomography (CT) imaging system 10 is shown as including a gantry 12 representative of a "third generation" CT scanner.

Gantry 12 has an x-ray source 14 that projects a beam of x-rays 16 toward a detector assembly 18 on the opposite side of the gantry 12. Detector assembly 18 is formed by a plurality of detectors 20 which together sense the projected x-rays that pass through a medical patient 22. Each detector 20 produces an electrical signal that represents not only the intensity of an impinging x-ray beam but is also capable of providing photon or x-ray count data, and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 receives data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 having a keyboard to input data parameters. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48.

While in the present discussion reference is made to a CT imaging system in which a source and detector rotate on a gantry arrangement, it should be borne in mind that the present technique is not limited to data collected on any particular type of scanner. For example, the technique may be applied to data collected via a scanner in which an X-ray source and a detector are effectively stationary and an object is rotated, or in which the detector is stationary but an X-ray source rotates. Further, the data could originate in a scanner in which both the X-ray source and detector are stationary, as where the X-ray source is distributed and can generate X-rays at different locations. Similarly, while generally circular scan geometries are discussed, other geometries may be envisioned as well. Further, the present technique could apply to three-dimensional or cone beam acquisitions as well as to two-dimensional acquisitions.

Figure 3:
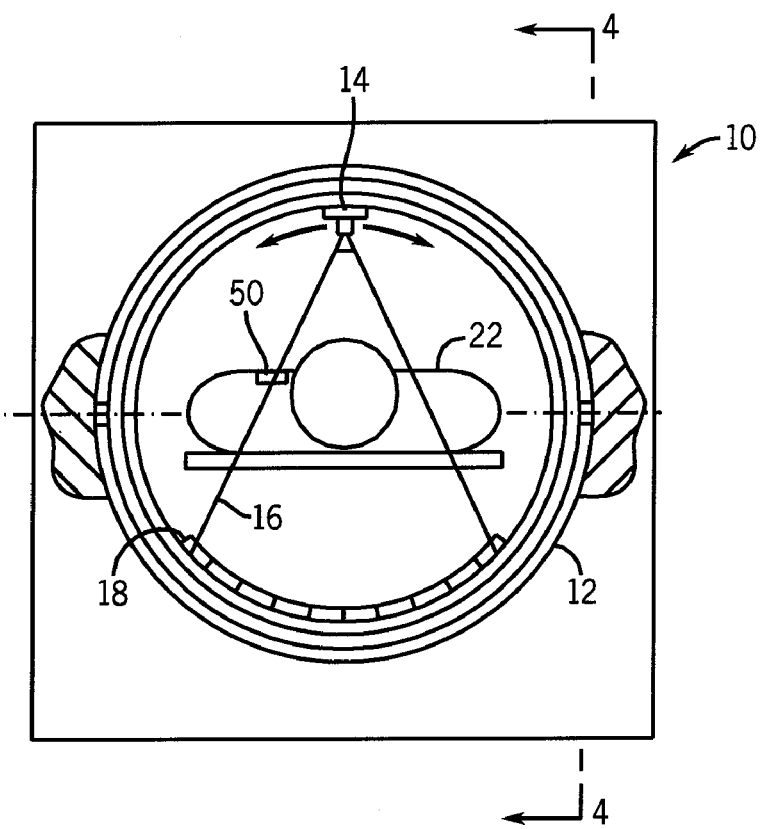
FIG. 3 is a cross-sectional end view of the CT imaging system of FIG. 1.

Referring now to FIG. 3, patient 22 is shown positioned in gantry opening 48 to receive x-ray beams 16 from x-ray source 14. A high density object 50 located in patient 22 is also shown. In many cases, the high density object is a metal object, such as dental fillings, prosthetic devices, or surgical clips. The presence of high density object 50 in the patient 22 causes the appearance of artifacts in an image reconstructed by image reconstructor 34. That is, high density object 50 causes strong attenuation of the x-ray beams 16 as they are projected through patient 22, thereby resulting in a reconstructed image with metal artifacts therein.

Figure 4:
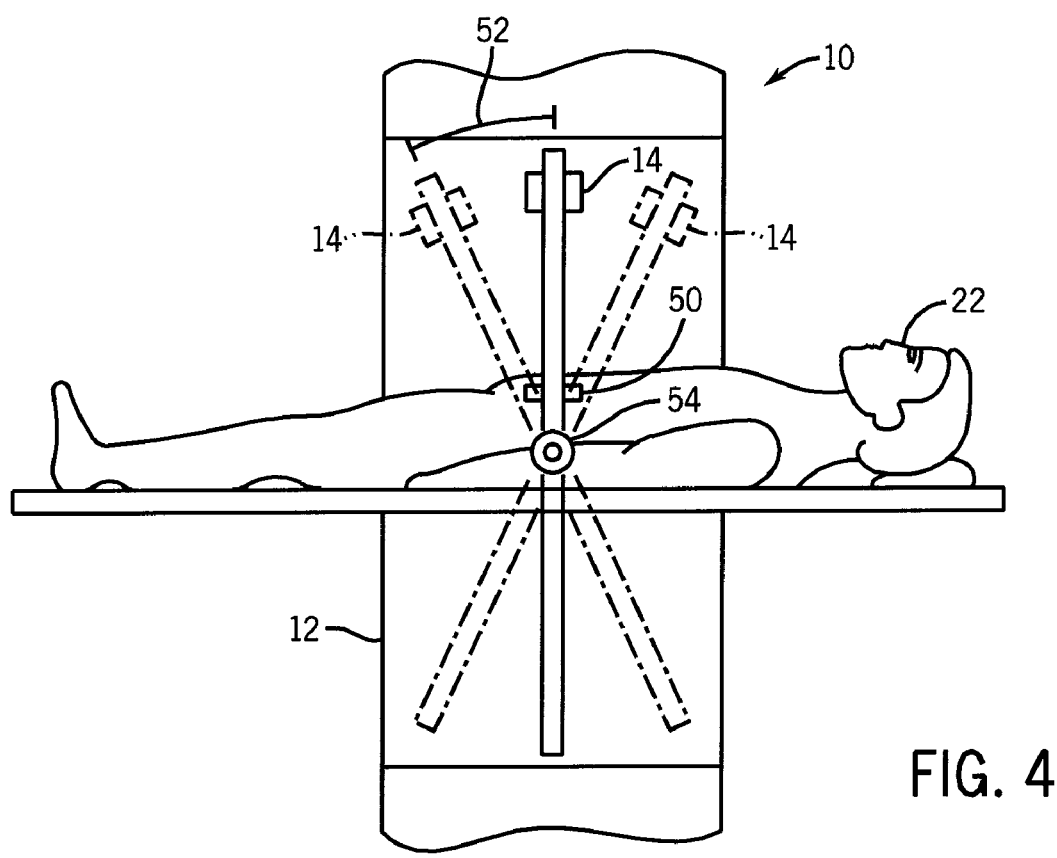
FIG. 4 is a side cross-sectional view of an embodiment of the CT imaging system of FIG. 1.

To correct this problem, multiple x-ray scans are performed at a plurality of different tilt angles 52. That is, x-ray beams 16 are emitted toward patient 22 at several different irradiation trajectories that provide different views and locations of the high density object 50 in the reconstructed image for each tilt angle 52. In one embodiment of the current invention, as shown in FIG. 4, gantry 12 is configured to tilt at a plurality of axial tilt angles 52 from a starting position as compared to z-axis 24 (see FIG. 1). Gantry 12 pivots about connection points 54 to tilt angles 52 in a positive and negative direction from the starting position. At each of these angles, x-ray source 14 rotates about the patient 22 by way of gantry rotation and emits x-ray beams 16 to acquire CT projection data from the patient 22. The exact number of tilt angles 52 at which additional x-ray scans are performed can vary, although typically this number of tilt angles will be between two and four.

In another embodiment of the present invention, it is envisioned that multiple x-ray sources 14 be included in CT imaging system 10 to acquire CT data at a plurality of irradiation angles 52. That is, rather than having a gantry 12 configured to tilt to a plurality of irradiation angles 52, CT imaging system 10 can include x-ray sources 14 positioned at multiple axial angles 52. As shown in FIG. 3, additional x-ray sources 14 (shown in phantom) are positioned at tilt angles 52 to provide different views and locations of the high density object 50 in the reconstructed image. Each of the x-ray sources 14 functions separately to emit a fan beam or cone beam of x-rays 16 to provide CT projection data at a plurality of complimentary irradiation angles 52. The x-ray source 14 at each of these tilt angles 52 rotates about the patient by way of gantry 12 rotation about center of rotation 24 and emits x-ray beams 16 to acquire CT projection data from the patient 22.

In another embodiment, the region of interest that is to be imaged of patient 22 is tilted manually. For example, in a cranial CT scan, the head of patient 22 is tilted to several different angles and a scan is performed at each of these angles. As compared to a configuration that includes a tiltable gantry or multiple x-ray sources, it is difficult to achieve precisely desired tilt/irradiation angles when manually tilting the head. As such, it is envisioned that the head can be roughly positioned to a desired angle and a positioning device (not shown) be attached thereto to provide exact angular and spatial position. Alternatively, fiducial markers can be used to determine the respective positions of the patient or of the region-of-interest.

It is also envisioned that, in addition to the x-ray beams 16 being emitted at several irradiation angles 52 from x-ray source 14, the x-ray scans can also be performed at different energy levels. That is, in one embodiment of the current invention, at least one of the x-ray scans is conducted at a different peak kilovoltage (kVp) level, which changes the peak and spectrum of energy of the incident photons comprising the emitted x-ray beams 16. With a scan performed at this different kVp level, an operator can achieve material decomposition and multiple material beam hardening correction.

Figure 5:
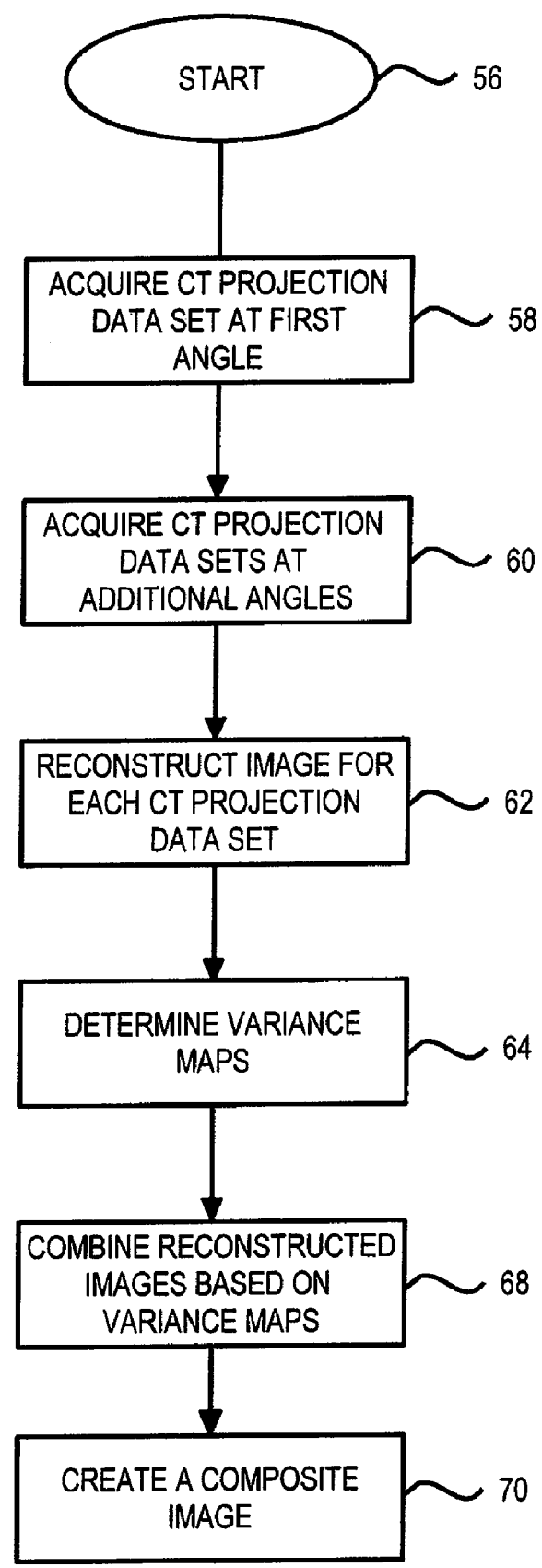
FIG. 5 is a flow chart setting forth one exemplary technique used to reduce metal artifacts in CT imaging in accordance with one embodiment of the present invention.

Upon acquisition of CT projection data at a plurality of tilt angles 52, and optionally at different energy (kVp) levels, computer 36 then processes the acquired data to construct a CT image that reduces or eliminates unwanted metal artifacts. As shown in FIG. 5, computer 36 is configured to carry out a series of process steps to produce a composite image of a region of interest in patient 22. This composite image will, ideally, eliminate beam hardening, measurement noise, and other image degradations factors caused by high density object 50.

Referring now to FIG. 5, a technique to create a composite image is shown for one embodiment of the invention. The technique illustrates one process for practicing the invention as well as illustrating implementation by computer. The technique begins 56 by acquiring 58 a CT projection data set at a first angle. Additional CT scans are then performed 60 at additional tilt angles to acquire additional CT projection data sets, with each of these CT projection data sets including sinogram elements therein.

A plurality of CT projection data sets are thus acquired from the x-ray scans performed at each of the different tilt angles. Once this plurality of projection data sets has been acquired, an image is reconstructed 62 for each of these data sets. The reconstruction for each of these CT projection data sets can be performed in a variety of ways well known in the art, although it is envisioned that adaptive filtration, interpolation methods, or iterative algorithms may be used. Regardless of the reconstruction method, the reconstructed image from each CT projection data set can be further improved by introducing sophisticated algorithms, such as projection completion FBP and adaptive filter FBP algorithms.

Each of the reconstructed images will display metal artifacts in different locations. That is, as each of the CT projection data sets is acquired from an x-ray scan performed at a different tilt angle, the metal artifact will appear in a different position in the reconstructed image for each tilt angle. Each of these separately reconstructed images from the projection data sets are then combined 68 by fusing or merging the images or the image data in an effort to minimize the effect of the artifact in a composite CT image. In one embodiment, data fusion includes combining the reconstructed images from each of the multiple tilting-gantry scans based on variance maps. The variance maps indicate the degree of uncertainty or the degree of error associated with an image pixel/voxel, based on the acquisition protocol, the scanned object, the measurement noise and the imaging configuration. The pattern of the metal artifacts in the reconstructed images is closely related to the x-ray scanning locus and the CT projection data associated therewith. Thus, the metal artifacts pattern will differ for each tilt/irradiation angle and these differences can be quantified using variance maps 64 (i.e., variance images) as calculated by way of sinogram elements in the projection data sets. The variance maps for each tilt/irradiation angle can be used to distinguish between the true image value and an image value corrupted by metal artifacts. Various data fusion or weighting schemes can be employed to eliminate the metal artifacts and improve image quality.

The variance map is a map of variance in the reconstructed images $f$ and is a good measurement of the noise in the images. To compute the variance map, a variance for each of a plurality of sinogram elements in the CT projection data sets is calculated. In performing these calculations, the readout number of x-ray count data from detectors 20 (i.e., input measurements) are first replaced by an estimate of the signal variance. For x-ray CT, this can be done by assuming that the readout numbers are Poisson random variables, or for high-count rate CT, that the measurements are Normal with a standard deviation equal to the square root of the mean signal. The exact relationship between the measurement and the estimate of the measurement variance depends on the exact processing stages involved in handling the measurement data prior to reconstruction. For an x-ray CT, the variance of the readout number (photon count N) can be given as:

$$Var_N = \lambda \approx N \quad \text{[Eqn. 1]},$$

where $\lambda$ is the parameter of Poisson process and N is the actual signal or photon count received by the detector channel.

In practical cases $\lambda$ is unknown. To calculate Var, N can be used to approximate $\lambda$, as $\lambda \approx N$ when N is not small. Thus the variance of projection data proj used for image reconstruction can be calculated as follows:

$$Var_{proj} = \left(\frac{\partial proj}{\partial N}\right)^2 \quad \text{[Eqn. 2]}$$

$$Var_N = \left(\frac{\partial(\ln(N_0/N))}{\partial N}\right)^2$$

$$Var_N \approx \frac{1}{N^2}$$

$$N = \frac{1}{N_0}$$

$$\frac{N_0}{N} = \frac{e^{proj}}{N_0}.$$

The images of the CT projection data, after being processed with an original filtered weighted backprojection algorithm, is:

$$f = h_1 \times weight_1 \times proj_1 + h_2 \times weight_2 \times proj_2 + \ldots + h_n \times weight_n \times proj_n \quad \text{[Eqn. 3]},$$

where h is the ramp filter, and weight is the weighting function.

The set of variances $Var_{proj}$ is then processed to form the variance map. The processing that takes place includes weighting, filtering, and backprojection steps. Weighting steps are "squared". (i.e., if the original reconstruction algorithm used to form the reconstructed image required that each measurement be weighted by a factor weight, then to calculate the variances, the measurement is weighted by weight*weight.) For filtering, impulse responses are "squared". (i.e., if the original reconstruction algorithm required that one convolve the measurements with a sequence (impulse response) h(n), then to calculate the variances, one convolves with h(n)*h(n).) Backprojection weightings are also "squared". (i.e., if the backprojection step in the reconstruction requires that projection data proj be updated, then to calculate the variances, one takes proj*proj=$Var_{proj}$.) Then from the relation between proj and $f$, the $Var_f$ can be calculated as:

$$Var_f = h_1^2 \times weight_1^2 \times Var_{proj_1} + h_2^2 \times weight_2^2 \times V_{proj_2} + \ldots + h_n^2 \times weight_n^2 \times Var_{proj_n} \quad \text{[Eqn. 4]}.$$

With these modifications, the original weighted filtered backprojection algorithm is transformed into an algorithm that will compute voxel variances (assuming that it is fed the variance of the measurements as input rather than the original data). Furthermore, changing the weighting factors and squaring the filter impulse response can typically be done ahead of time, resulting in no change in the computational cost of the process. It is envisioned that these steps apply to CT reconstruction algorithms from any geometry (2D, 3D, 4D, axial, helical, etc.) that comprise these steps. As such, pixel variance, or other image data point variance, can be determined rather than voxel variance, From the variance map obtained above using Eqns. 1-4, the combining 68 of the CT projection data images is then based on a determined minimum variance between the CT projection data images. As an example, images for scans performed at two different tilt angles can be described as follows:

$$f(x) = \alpha f_1(x) + (1-\alpha)f_2(x), \, 0 \leq \alpha \leq 1 \quad \text{[Eqn. 5]}$$

$$Var_f = \alpha^2 Var_{f1} + (1-\alpha)^2 Var_{f2} \quad \text{[Eqn. 6]}.$$

The minimum of $Var_f$ will be achieved when:

$$a = \frac{Var_{f2}}{Var_{f1} + Var_{f2}}. \quad [\text{Eqn. 7}]$$

Thus, data fusion is implemented as:

$$f(x) = \frac{Var_{f2}}{Var_{f1} + Var_{f2}} f_1(x) + \frac{Var_{f1}}{Var_{f1} + Var_{f2}} f_2(x) \quad [\text{Eqn. 8}]$$

Upon the calculation of the variance map 64 and the minimum variance of each of the plurality of voxels as determined therefrom, the separate images for each of the CT projection data sets are merged 68. Image reconstructor 34 and computer 36 then create 70 a composite image from the merged CT projection data images. This composite image will be substantially free of artifacts caused by the high density object 50. The amount of artifact reduction in the composite image will be, in large part, determined by the number of scans performed. That is, a composite image combining images of CT projection data sets acquired at four distinct tilt angles 52 will eliminate a greater amount of metal artifacts than the combination of only two images.

While a method of combining the CT projection data images by way of variance maps and minimum voxel variance has been described above, it is also envisioned that other methods of combining the images can be employed. For example, morphological operations (where information from neighboring pixels is used to refine pixel values) can be used to combine the images by way of spatial filters or spatial Markov random field priors.

An iterative technique can also be employed to combine the CT projection data images based on the combined measured sinograms of the CT projection data sets. In this process, the statistical properties of the data sets are included to improve the combination of the images to reduce metal artifacts in the combined images. In this case, the step of computing separate images for each tilt angle and then combining the different images can be eliminated. Instead, iterative reconstruction can directly reconstruct an aggregate image (optimal according to the iterative recon cost function) from all the datasets obtained at different tilt angles. This is achieved by incorporating the scanner acquisition geometry and scan protocol along with the actual tilt angles in the forward model, as will be obvious to anybody that is skilled in the art of iterative reconstruction.

As will be appreciated by those skilled in the art, a sinogram is a collection of output data from the detector array 18 resulting from radiation attenuated by patient 22 at a given x-ray source 14 position. The output data from each x-ray source 14 and detector 20 position or view corresponds to a row of projection data in the sinogram. As used herein, the term projection data is sometimes referred to as measured sinogram data. The measured sinogram data is representative of a plurality of sinogram elements. Thus, each row of the sinogram constitutes a projection view that is indicative of the attenuation information for a distinct view angle, for given source and detector positions, with respect to patient 22. These projection views are then processed to generate reconstructed image data (cross-sectional images) of the patient 22 at the given position.

The technical effect of the technique described above, which is performed by a computer program stored on a computer readable storage medium, is to reduce artifacts in image data caused by high density objects.

Therefore, according to one embodiment of the present invention, a computer readable storage medium includes a computer program to adaptively control a CT system for reconstructing an image with reduced artifacts caused by a high density object in a scanned region of interest. The computer program represents a set of instructions that, when executed by a computer, causes the computer to perform a plurality of x-ray scans at a plurality of tilt angles, acquire a plurality of projection data sets from the plurality of x-ray scans, combine the plurality of projection data sets, and reconstruct a composite image from the combined image data sets.

According to another embodiment of the present invention, a method of reducing metal artifacts in CT imaging includes the steps of acquiring CT projection data of a region of interest at each of a number of differing irradiation angles, and combining the CT projection data acquired at each of the number of different irradiation angles so as to reduce metal artifacts in a resulting image.

According to yet another embodiment of the present invention, a CT imaging system to reduce metal artifacts includes a CT imaging apparatus. The CT imaging apparatus has a data acquisition module that includes a gantry having a bore designed to receive a patient therethrough, and wherein the gantry has at least one x-ray source and an x-ray detector disposed therein to emit x-rays toward the patient and receive x-rays attenuated by the patient, respectively. The CT imaging apparatus further includes a computer programmed to acquire CT projection data at a number of tilt angles and merge the CT projection data to create an aggregate image. The merging of the CT projection data is based on one of a variance map, morphological operations, and an iterative reconstruction process.

The present invention has been described in terms of the preferred embodiment, and it is recognized that equivalents, alternatives, and modifications, aside from those expressly stated, are possible and within the scope of the appending claims.

What is claimed is:

1. A method of reducing metal artifacts in CT imaging comprising:
    performing a first scan to acquire first CT projection data of a region of interest at a first irradiation angles maintained for the duration of the first scan;
    performing a second scan to acquire second CT projection data of the region of interest at a second irradiation angle maintained for the duration of the second scan; and
    combining the first and second CT projection data acquired at each of the first and second irradiation angles so as to reduce metal artifacts in a resulting image.

2. The method of claim 1 wherein the step of combining includes fusing reconstructed images in a post-processing algorithm that minimizes artifacts appearing in different regions of each reconstructed image of the region of interest.

3. The method of claim 1 wherein the combining of CT projection data includes at least one of a variance estimate of sinogram elements in a given data set, a morphological operations process, and an iterative reconstruction process.

4. The method of claim 3 wherein if the combining of CT image data includes a variance estimate of sinogram elements in a given data set, then the combination further includes determining statistical properties of the CT projection data as applied to the sinogram elements.

5. The method of claim 3 wherein if the combining of CT image data includes a variance estimate of sinogram elements in a given data set, then the combination further includes a rapid variance calculation that includes replacing input measurements with an estimate of signal variance.

6. The method of claim 5 further comprising deriving a set of variance estimates and forming a variance image from the set of variance estimates.

7. The method of claim 6 further comprising implementation of a weighted-filtered-backprojection reconstruction algorithm wherein the variance estimates are calculated by squaring each weight, convolving a square of a filter response, and adding a square of backprojection weightings.

8. The method of claim 1 wherein the first and second irradiation angles are achieved by at least one of tilting a CT apparatus gantry, adjusting the region of interest to another tilt angle with respect to a given plane, and implementing a CT apparatus having multiple sources that provide multiple complementary scan trajectories.

9. The method of claim 1 further comprising adjusting energy level based on an angle of irradiation to perform material decomposition and multiple material beam hardening correction.

10. A CT imaging system to reduce metal artifacts comprising:
a CT imaging apparatus comprising a data acquisition module including a gantry having a bore designed to receive a patient therethrough, the gantry having at least one x-ray source and an x-ray detector disposed therein to emit x-rays toward the patient and receive x-rays attenuated by the patient, respectively, the CT imaging apparatus further comprising a computer programmed to:
acquire CT projection data at a plurality of different tilt angles;
merge the CT projection data to create an aggregate image; and
wherein the merging is based on one of a variance map, morphological operations, and an iterative reconstruction process.

11. The CT imaging system of claim 10 wherein the computer is further programmed to:
reconstruct an image from the CT projection data at each of the number of tilt angles; and
merge the images to create an aggregate image.

12. The CT imaging system of claim 10 wherein the computer is further programmed to merge the CT projection data based on a minimum variance of sinogram elements, as determined by the variance map.

13. The CT imaging system of claim 10 wherein the gantry is configured to tilt at a plurality of angles to emit a fan beam of x-rays toward the patient at the number of tilt angles.

14. The CT imaging system of claim 10 wherein the at least one x-ray source further comprises a plurality of x-ray sources positioned to emit x-ray beams at each of the plurality of tilt angles.

15. The CT imaging system of claim 10 wherein the computer is further programmed to perform at least one of the plurality of x-ray scans at a different energy level.

16. The CT imaging system of claim 10 wherein the computer is further programmed to perform an iterative reconstruction process based on combined measured sinograms and statistical properties of the CT projection data.

* * * * *

UNITED STATES PATENT AND TRADEMARK OFFICE
CERTIFICATE OF CORRECTION

| | | |
|---|---|---|
| PATENT NO. | : 7,548,604 B2 | Page 1 of 1 |
| APPLICATION NO. | : 11/620004 | |
| DATED | : June 16, 2009 | |
| INVENTOR(S) | : De Man et al. | |

It is certified that error appears in the above-identified patent and that said Letters Patent is hereby corrected as shown below:

In Column 6, Lines 45-46, in Equation (4), delete " $Var_f = h_1^2 \times weight_1^2 \times Var_{proj_1} + h_2^2 \times weight_2^2 \times V_{proj_2} + \ldots + h_n^2 \times weight_n^2 \times Var_{proj_n}$ " and insert -- $Var_f = h_1^2 \times weight_1^2 \times Var_{proj_1} + h_2^2 \times weight_2^2 \times Var_{proj_2} + \ldots + h_n^2 \times weight_n^2 \times Var_{proj_n}$ --, therefor.

In Column 6, Line 59, delete "variance," and insert -- variance. --, therefor.

In Column 6, Line 65, in Equation (5), delete " $f(x) = \alpha f_1(x) + (1-\alpha) f_2(x), 0 \leq \alpha \leq 1$ ," and insert -- $f(x) = af_1(x) + (1-a)f_2(x), 0 \leq a \leq 1$ --, therefor.

In Column 6, Line 67, in Equation (6), delete " $Var_f = \alpha^2 Var_{f1} + (1-\alpha)^2 Var_{f2}$ " and insert -- $Var_f = a^2 Var_{f1} + (1-a)^2 Var_{f2}$ --, therefor.

Signed and Sealed this
Eighteenth Day of September, 2012

David J. Kappos
*Director of the United States Patent and Trademark Office*